(12) United States Patent
March (10) Patent No.: US 7,131,839 B2
(45) Date of Patent: Nov. 7, 2006

(54) BACKFLOW PREVENTION SLEEVE FOR SUCTIONING DEVICES

(76) Inventor: Michael S. March, 32092 State 27, Long Prairie, MN (US) 56347

(*) Notice: Subject to any disclaimer, the term of this patent is extended or adjusted under 35 U.S.C. 154(b) by 0 days.

(21) Appl. No.: 11/057,326

(22) Filed: Feb. 11, 2005

(65) Prior Publication Data

US 2005/0175961 A1 Aug. 11, 2005

Related U.S. Application Data

(60) Provisional application No. 60/543,789, filed on Feb. 11, 2004.

(51) Int. Cl.
*A61C 17/14* (2006.01)
(52) U.S. Cl. .......................... 433/95; 433/91
(58) Field of Classification Search ................. 433/91, 433/95, 96, 116, 115; 604/902, 131, 35; 15/300.1
See application file for complete search history.

(56) References Cited

U.S. PATENT DOCUMENTS

| | | | |
|---|---|---|---|
| 3,417,750 A * | 12/1968 | Carson | 604/185 |
| 3,476,144 A | 11/1969 | Krantz | |
| 4,015,336 A | 4/1977 | Johnson | |
| 4,081,176 A | 3/1978 | Johnson | |
| 4,222,407 A | 9/1980 | Ruschke et al. | |
| 4,522,592 A | 6/1985 | Johnson | |
| 4,526,573 A | 7/1985 | Lester et al. | |
| 4,580,978 A | 4/1986 | Motola et al. | |
| 5,076,787 A | 12/1991 | Overmyer | |
| 5,114,342 A | 5/1992 | Young et al. | |
| 5,165,891 A | 11/1992 | Young et al. | |
| 5,228,851 A * | 7/1993 | Burton | 433/116 |
| 5,230,625 A | 7/1993 | Sutter et al. | |
| 5,267,586 A | 12/1993 | Jankavaara | |
| 5,267,860 A * | 12/1993 | Ingram et al. | 433/116 |
| 5,425,637 A | 6/1995 | Whitehouse et al. | |
| 5,441,410 A | 8/1995 | Segerdal | |
| 5,464,397 A | 11/1995 | Powers Jr. | |
| 5,509,802 A | 4/1996 | Whitehouse et al. | |
| 5,725,374 A | 3/1998 | Young | |

(Continued)

OTHER PUBLICATIONS

"Possibility of Cross-Contamination Between Dental Patients by Means of the Saliva Ejector," C.M. Watson, R.L.S. Whitehouse, JADA, vol. 124, pp. 77-80, Apr. 1993.

(Continued)

*Primary Examiner*—Cary E. OConnor
(74) *Attorney, Agent, or Firm*—Patterson, Thuente, Skaar & Christensen P.A.

(57) ABSTRACT

A sleeve for preventing backflow and cross-contamination between patients of fluid and particulate matter as well as other contaminants present within a dental/medical suctioning device. The sleeve includes a sleeve inlet end that sealingly attaches to and surrounds at least a portion of the suctioning device the vacuum hose to the evacuator tip. The sleeve also has a sleeve exhaust end that is inserted into the control valve and can reside within the interior lumen of the vacuum hose during normal suction operation. During operation, the sleeve provides a seal between the patient contact part and the control valve of the suctioning device. The proximate end collapses, seals, and/or provides a barrier when the suctioning device does not draw a vacuum away from the patient and towards the vacuum source.

22 Claims, 6 Drawing Sheets

U.S. PATENT DOCUMENTS

| | | | |
|---|---|---|---|
| 5,728,078 A | 3/1998 | Powers, Jr. | |
| 5,741,134 A | 4/1998 | Davis | |
| 5,769,702 A * | 6/1998 | Hanson | 454/63 |
| 5,855,478 A | 1/1999 | Van | |
| 5,882,194 A | 3/1999 | Davis et al. | |
| 5,944,522 A | 8/1999 | Lonczak et al. | |
| 6,068,476 A | 5/2000 | Point | |
| 6,203,321 B1 | 3/2001 | Helmer et al. | |
| 6,402,511 B1 * | 6/2002 | Calderwood | 433/29 |
| 6,821,118 B1 | 11/2004 | Schlussel | |
| 2003/0219696 A1 | 11/2003 | Moreland | |
| 2004/0014002 A1 | 1/2004 | Lundgren | |

OTHER PUBLICATIONS

*Backflow in Low-Volume Suction Lines: The Impact of Pressure Changes*, G. Mann, T. Campbell and J. Crawford, JADA, vol. 127, pp. 611-615, May. 1996.

"Cross-Contamination Potential of Saliva Ejectors Used in Dentistry," J. Barbeau, et al., Journal of Hospital Infection, vol. 40, pp. 303-311, 1998.

*Guidelines for Infection Control in the Dental Health Care Setting-2003*, Center for Disease Control, 97 pgs., 2003.

Website Print-out: CROSSTEX™ International; Disposables for the Healthcare Profession, 1 pg.; Jul. 8, 2005.

* cited by examiner

BACKFLOW PREVENTION SLEEVE FOR SUCTIONING DEVICES

PRIORITY CLAIM

The present application claims priority to U.S. Provisional Application No. 60/543,789 filed Feb. 11, 2004, and entitled, "BACKFLOW PREVENTION SLEEVE FOR SUCTIONING DEVICES," which is herein incorporated by reference to the extent not inconsistent with the present disclosure.

FIELD OF THE INVENTION

The invention relates generally to suction devices used in healthcare and health maintenance. More particularly, the invention relates to a sleeve for use with dental and medical suction devices that prevents cross-contamination or cross-exposure of various types of fluid and particulate matter as well as other contaminants between patients.

BACKGROUND OF THE INVENTION

Suction systems are commonly used in dental practices, medical clinics, hospitals, and other medical operations to remove contaminated debris consisting daily in the dental office of: saliva, food debris, tarter, stain, dental bacterial plaque, tooth debris, filling debris, mucous, phlegm, blood, cleaning chemicals, and less frequently pus, vomit and chemicals spills. In the case of a dental practice, a dental suction system can comprise a vacuum pump, a separator tank, an amalgam separator, a vacuum feed line and a hand-operable suction device (evacuator) in the treatment room. The evacuator is comprised of a vacuum tip, control valve and vacuum hose. Suction systems can comprise relatively small systems for use by a single practitioner or may comprise large, centralized systems allowing for simultaneous operation within a plurality of treatment rooms. Examples of representative dental suction systems include systems as manufactured and sold by companies such as, for example, RAMVAC®, Apollo Dental Products®, A-dec, etc.

It has been recognized in the art that cross-contamination between patients, for example, dental patients, can occur when evacuators (suctioning devices) attached to vacuum lines are used to remove such bodily fluids and contaminants. Various articles, guidelines and studies have addressed the potential for such cross-contamination including: "*Possibility of Cross-Contamination Between Dental Patients by Means of the Saliva Ejector,*" C. M. Watson, R. L. S. Whitehouse, JADA, Vol. 124, April 1993; "*Backflow in Low-Volume Suction Lines: The Impact of Pressure Changes,*" G. Mann, T. Campbell and J. Crawford, JADA, Vol. 127, May 1996; "*Cross-Contamination Potential of Saliva Ejectors Used in Dentistry,*" J. Bargeau, et al., Journal of Hospital Infection, 1998: 40:303–11; and "*Guidelines for Infection Control in the Dental Health Care Setting*-2003, Center for Disease Control, 2003, all of which are herein incorporated by reference to the extent not inconsistent with the present disclosure. Such cross-contamination can occur as vacuumed bodily fluids and/or contaminants can backflow from the vacuum line into the patient's mouth/body. Backflow can occur for a variety of different reasons. For instance, if the intake is blocked disrupting vacuum flow, the contaminated fluid in the vacuum line may flow down by gravity if the suction device is tilted down toward the patient. Also, flow can be interrupted if the patient closes their mouth over the vacuum tip stopping flow or even overpowering the vacuum by sucking on the tip. In other instances, the suction device can be left tilted down inside of the patient after the control valve is closed. In yet other instances, the vacuum line or hose distal to the vacuum tip and control valve can become obstructed during use creating a temporary loss of suction flow. Finally, the vacuum source, i.e., the vacuum pump can stop, which is further aggravated if there is a vertical vacuum feed line from the ceiling that can drain down into the vacuum tube tip.

Backflow fluid can contain a variety of unwanted contaminated debris consisting daily in the dental office of: saliva, food debris, tarter, stain, dental bacterial plaque, tooth debris filling debris, mucous, phlegm, blood, cleaning chemicals, and less frequently pus, vomit and medical spills as well as microbes such as bacteria, viruses, and fungi. In some instances, microbes can travel in a reverse direction through the suctioning device in an airborne form without the assistance of a fluid carrier. Due to the potential presence of communicable diseases within the vacuum line, there is a need to provide maximum protection against cross-contamination between patients.

A variety of prior art devices have attempted to prevent the cross-contamination risk that is inherent in suctioning devices. In some instances, various valve designs have been contemplated for use in the suctioning device that would prevent backflow. However, such valves can be complex, expensive, and difficult to fully clean, disinfect, and sterilize. In other instances, parts, which come into direct contact with the patient during the performed procedure, have been designed and manufactured to be disposable and replaceable so as to attempt to place a buffer zone between the patient and contaminated portions of the suctioning valve and hose. These disposable and replaceable vacuum tips can be subject to allowing backflow in the event of a loss in suction flow and/or serve only as a buffer zone that can be quickly breached. Additionally, even if the portion of the suctioning device that comes into contact with the patient during the performed procedure is replaced for each new patient, it is generally too expensive and time-consuming to replace the vacuum hose and control valve.

Regardless of component design, the vacuum hose is difficult to properly clean and sterilize due to temperature and chemical compatibility constraints resulting in residual fluid in the vacuum hose that can lead to the exchange of unwanted and/or dangerous externally introduced fluids from prior patients. Further, it is very difficult to properly clean (scrub and rinse) contaminants from the inside of a hose, which is needed before it can be effectively disinfected and then sterilized. Additionally, the control valve attached to the hose is difficult to remove, disassemble, clean, autoclave, and reassemble. Also, sterilizing the control valve is fruitless after reattaching it to a contaminated hose. Therefore, when a new disposable/replaceable end of the dental/medical suctioning device is inserted onto the vacuum line, the patient is still at risk of being exposed to backflow or reverse traveling movement of microbes. Therefore, the current disposable and replaceable parts may provide a sense of false security to patients and practitioners.

Another disadvantage of the prior art with respect to disposable/replaceable parts is that it does not allow the operator to shut-off the vacuum and then restart it without subjecting the patient to cross-contamination from backflow as the evacuator is sloped down into the patient's mouth. Allowing the vacuum line to suck air from the general room is not a viable option as the portion of the suction device that is inserted into the patient may become contaminated from airborne contaminants. Further, a vacuum line allowed to suck air from the general room produces an unwanted and annoying hissing noise from the dental/medical suctioning device.

Therefore, there is a need for an efficient, cost-effective product that can be used with current dental/medical suctioning devices to prevent cross-contamination between patients. Such a product should allow the operator of the suctioning device to stop and restart the suctioning device without subjecting the patient to cross-contamination by backflow or having to replace any parts.

SUMMARY OF THE INVENTION

Accordingly, an objective and advantage of the present invention is the convenience, cost-efficiency, and effectiveness of a sleeve that prevents backflow of fluid matter and other contaminants in a dental/medical suctioning apparatus.

It is another object of the present invention to provide a sleeve that prevents cross-contamination of microbes between patients.

It is another object of the present invention to provide a sleeve that is disposable and replaceable.

Another object of the present invention is to provide a sleeve that allows the user of the suctioning device to start, stop, and restart the suctioning device more than one time without having to replace the portion of the suction device that comes into contact with the patient.

Another object of the present invention is to provide a sleeve that does not require any additional equipment, but can be used with a practitioner's normal evacuation system.

Another object of the present invention is to provide a sleeve that will not compromise the function of the dental/medical suctioning device.

Another object of the present invention is to provide a sleeve that is user-friendly and requires essentially no extra effort in preparing the replaceable/disposable tube for operating use.

Another object of the present invention is to provide a sleeve that shields the control valve from debris and contaminants and saves time and money in cleaning, disinfecting, and in the use of ineffective chemicals.

Another object of the present invention is to provide a sleeve that can be used with a dental saliva ejector.

A further object of the present invention is to provide a sleeve that can be used with a high volume evacuator.

A still further object of the present invention is to provide a sleeve that can be used in medical suction devices.

These and other features and advantages of the present invention will be further understood and apparent to a person of ordinary skill in the art by reference to the following specification, claims, and appended drawings.

DETAILED DESCRIPTION OF THE PREFERRED EMBODIMENTS

Embodiments of the present invention have wide applications to a number of dental and medical procedures and environments. Therefore, although preferred embodiments of the invention will be described with respect to dental devices and applications, the invention is not limited to these embodiments, but would be equally applicable to other medical applications in which eliminating cross-contamination in vacuum equipment is desired.

Figure 1:
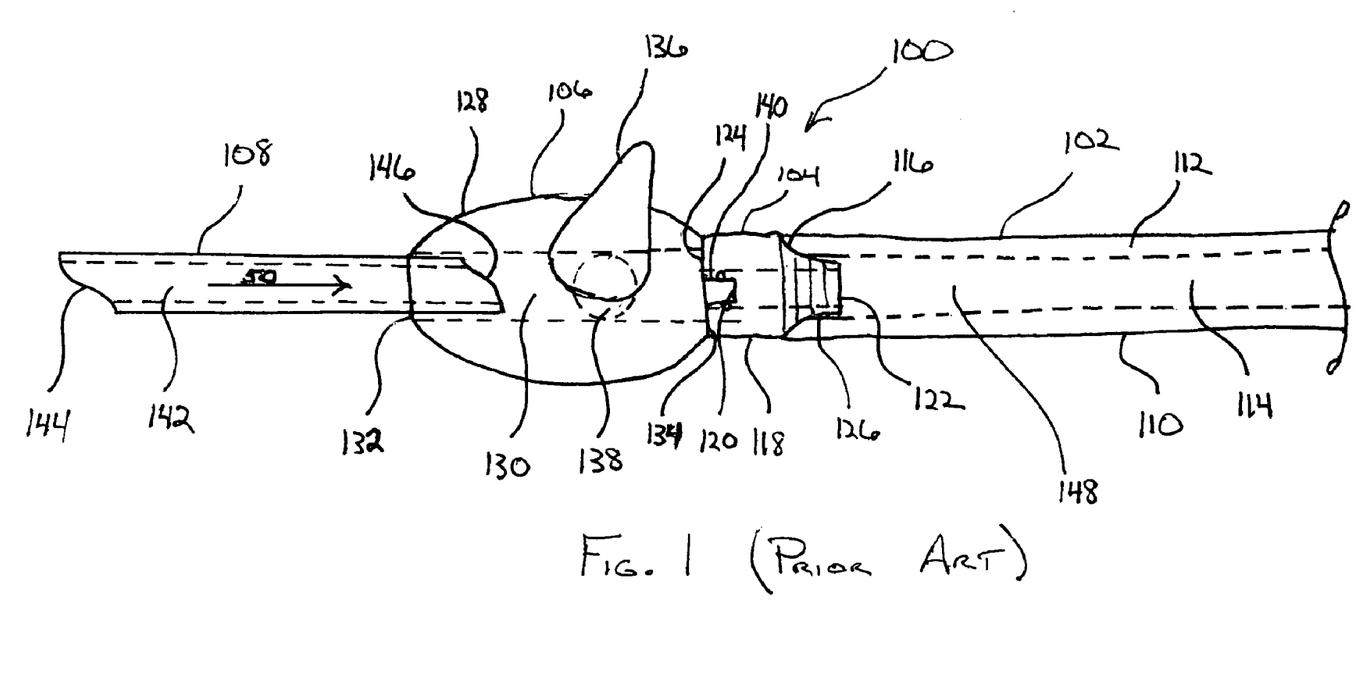
FIG. 1 is a partially hidden, side view of a prior art, hand-operable suction device or evacuator.

Referring now to the drawings, there is shown in FIG. 1, a hand-operable suction device 100 as presently used in the practice of dentistry. As illustrated in FIG. 1, the hand-operable suction device 100 comprises a vacuum line 102, a hose adapter 104, a control valve 106 and an evacuator tip 108. Though not depicted, it is to be understood that vacuum line 102 is ultimately fluidly connected to a suction system, i.e. vacuum source, for providing suction through the hand-operable suction device 100 as indicated by the suction flow arrow in FIG. 1. Evacuator tip 108 can comprise either a High Volume Evacuator (HVE) or a Low Volume Evacuator (saliva ejector). Evacuator tip 108 can be fabricated so as to be a disposable, one-time use instrument or can be fabricated to withstand a suitable sanitization/sterilization/cleaning process, such as autoclaving and/or chemical cleaning, so as to be reusable.

Vacuum line 102 generally comprises a flexible hose 110 having a hose wall 112 such that a hose lumen 114 is defined between a hose receiving end 116 and a vacuum attachment end (not depicted). Hose adapter 104 comprises an adapter body 118 having an adapter lumen 120 operably defined between a hose insertion end 122 and a valve attachment end 124. Hose insertion end 122 generally comprises a projection member 126 adapted for retainable insertion into hose receiving end 116. Projection member 126 can comprise threads, barbs, seals and/or other suitable retaining mechanisms, either individually or in combination, so as to define a leak-free connection between the vacuum line 102 and hose adapter 104.

Control valve 106 generally comprises a valve body 128 defining a valve lumen 130 between a tip receiving aperture 132 and an adapter connecting aperture 134. Valve body 128 comprises an actuator 136 for operably positioning a valve sealing member 138 within the valve lumen 130. Adapter connecting aperture 134 generally comprises a connecting member 140 for operably attaching the control valve 106 to the valve attachment end 124 of hose adapter 104. Evacuator tip 108 comprises an evacuator lumen 142 defined by an inlet end 144 and an exhaust end 146. Evacuator tip 108 has a generally circular cross-sectional appearance and is adapted such that exhaust end 146 is slidably insertable into the valve receiving end 134 of control valve 106.

When fully assembled, as shown in FIG. 1, hand-operable suction device 100 comprises a continuous suction lumen 148 defined by the hose lumen 114, adapter lumen 120, valve lumen 130 and evacuator lumen 142. During use in a dental procedure, a dentist or hygienist operates the actuator 136 such that valve sealing member 138 is selectively in either an open disposition wherein suction flow is allowed to flow into the inlet end 144 of the evacuator tip 108 and through the continuous suction lumen 148, or in a closed disposition wherein the valve sealing member 138 seals the valve lumen 130 such that no suction flow is allowed through the continuous suction lumen 146. In typical clinical settings, hand-operable suction device 100 may be flushed with water between patients and cleaned with a chemical rinse at the end of the day in an attempt to eliminate the backflow problems associated with hand-operable suction device 100.

Figures 2, 3:
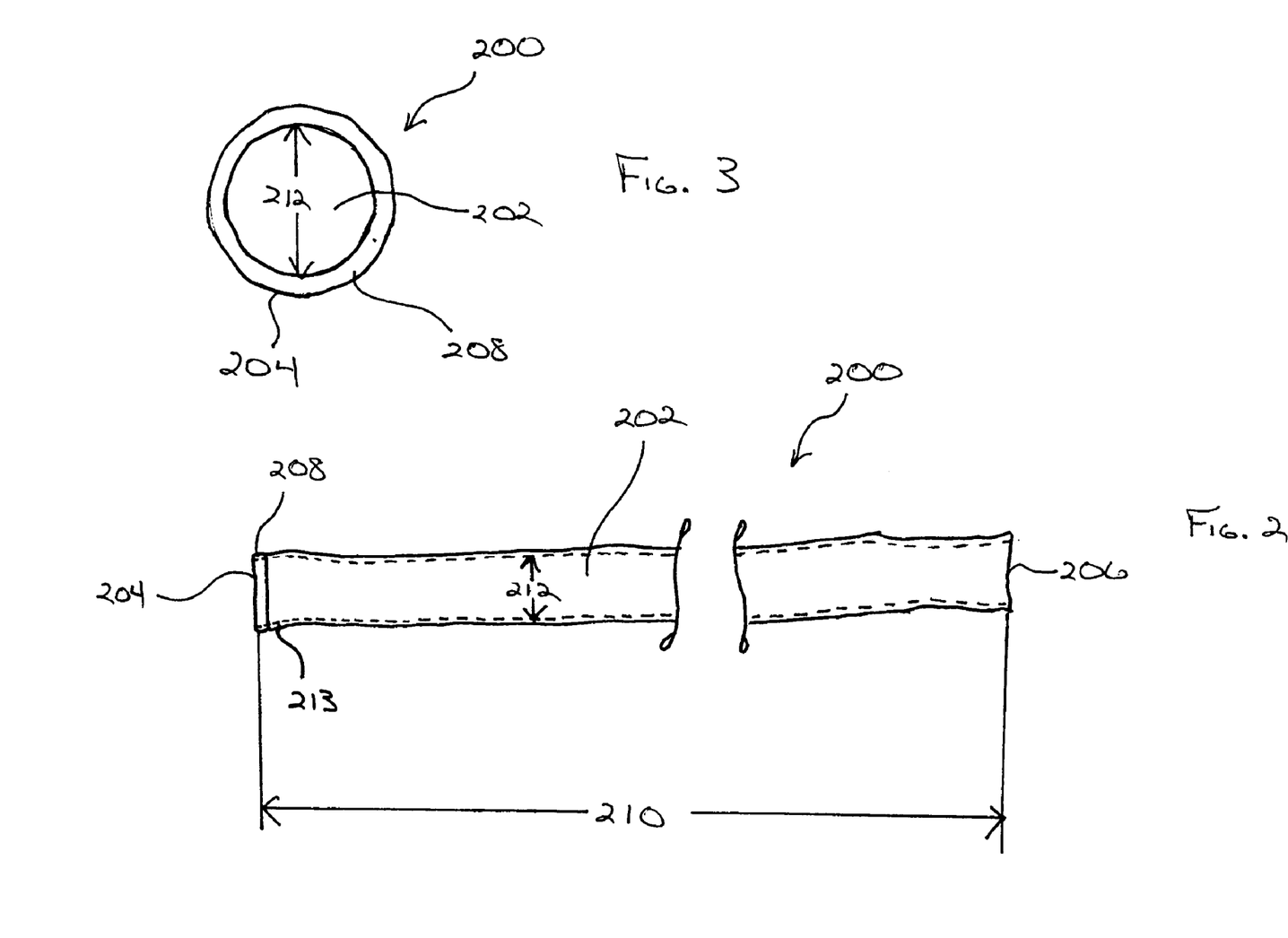
FIG. 2 is a partially hidden, side view of a backflow prevention sleeve of the present invention.
FIG. 3 is an end view of a sleeve inlet end of the backflow prevention sleeve of FIG. 2.

Referring primarily now to FIGS. 2 and 3, there is shown a presently preferred, representative embodiment of a backflow prevention sleeve 200. The backflow prevention sleeve 200 has a continuous sleeve lumen 202 defined between a sleeve inlet end 204 and a sleeve exhaust end 206. Sleeve inlet end 204 can comprise an annular ring 208 so as to define and distinguish sleeve inlet end 204 from sleeve exhaust end 206. Sleeve inlet end 204 and sleeve exhaust end 206 further define a sleeve length 210. Sleeve length 210 can comprise any suitable length such as, for example, from about two to about thirty inches in length. Backflow prevention sleeve 204 further comprises a sleeve diameter 212.

As depicted in FIGS. 2 and 3, sleeve 200 can comprise a shape resembling a cylindrical tube. Backflow prevention sleeve 200 can comprise elastic materials suitable for use in dental or medical applications such as, for example, a natural rubber such as, for example, latex rubber or a synthetic rubber-like material such as, for example, butyl rubber, ethylene/propylene rubber, fluorocarbon elastomers, choloprene, nitrile, vinyl, polybutadiene, silicone rubber, styrene-butadiene rubber and hydrogenated nitrile rubber. In addition to possessing elastic qualities, backflow prevention sleeve 200 can also be fabricated of materials that are nonabsorbent, nonadsorbent, and/or impermeable to liquids and gases. In some representative embodiments, backflow prevention sleeve 200 can comprise an elastomeric material that has antimicrobial properties such as antibiotics or antiseptics, which can clean, disinfect, sterilize and/or sanitize matter that comes into contact with the backflow prevention sleeve 200. In another representative embodiment, backflow prevention sleeve 200 can comprise an autoclavable material. In some representative embodiments, sleeve 200 can comprise a sleeve wall 213 having a wall thickness from about 0.1 mm to about 1.0 mm, and more preferably about 0.5 mm.

Figure 4:
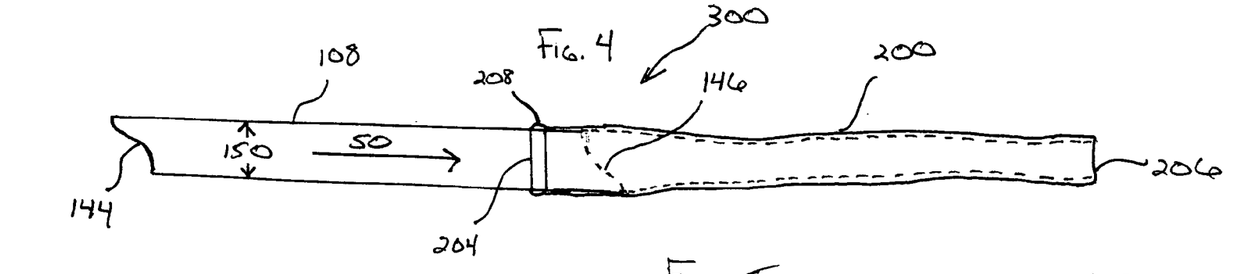
FIG. 4 is a partially hidden, side view of a backflow resistant evacuator tip.

As illustrated in FIG. 4, backflow prevention sleeve 200 can be attached to evacuator tip 108 to form a backflow resistant evacuator tip 300. Backflow resistant evacuator tip 300 can be formed by inserting exhaust end 146 of the evacuator tip 108 into the sleeve inlet end 204 of the backflow prevention sleeve 200. In a representative embodiment, sleeve diameter 212 is equal to or less than to an evacuator diameter 150 such that annular ring 208 must stretch to accommodate insertion of the exhaust end 146 resulting in a sealed interface between the backflow prevention sleeve 200 and the evacuator tip 108. In other alternative embodiments, backflow prevention sleeve 200 can be attached to the evacuator tip 108 through other suitable attachment methods such as, for example, thermal bonding, adhesive bonding and integral molding. In another representative embodiment, evacuator tip 108 can comprise an exterior annular ring, either indented or protruding, wherein the backflow prevention sleeve 200 can be positioned over the exterior, annular ring. In another alternative embodiment, the backflow prevention sleeve 200 can be coupled to the evacuator tip 108 using a suitable fitting which can be snapped or rolled over the evacuator tip 108.

Figure 5:
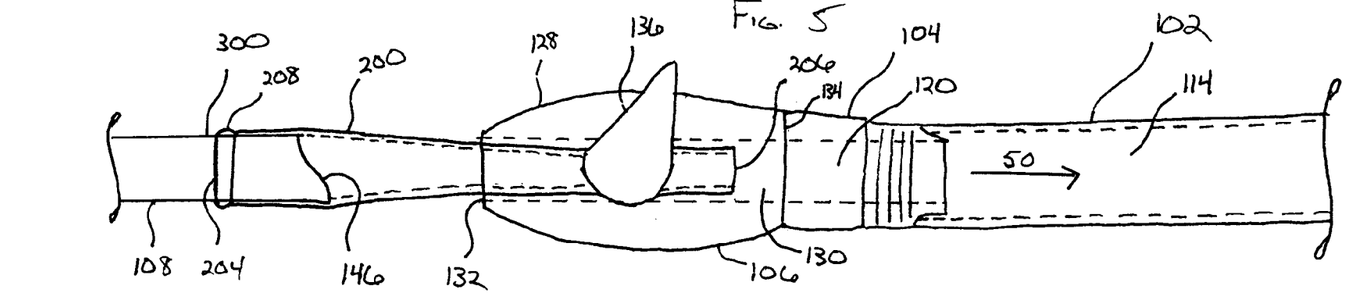
FIG. 5 is a partially hidden, side view of the backflow resistant evacuator tip of FIG. 4 being attached to a hand-operable suction device.
Figure 6:
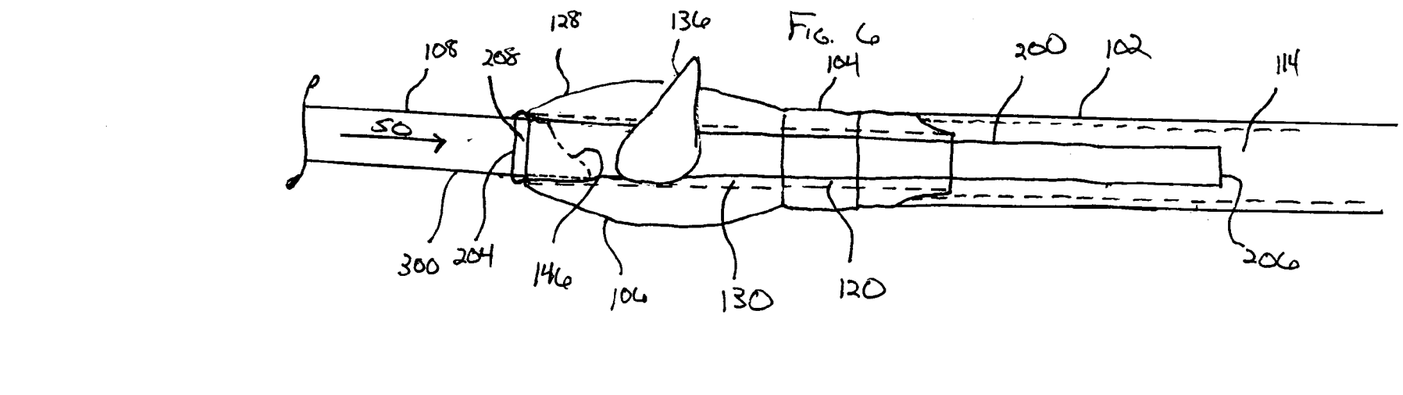
FIG. 6 is a partially hidden, side view of the backflow resistant evacuator tip of FIG. 4 operably attached to a hand-operable suction device.
Figure 7:
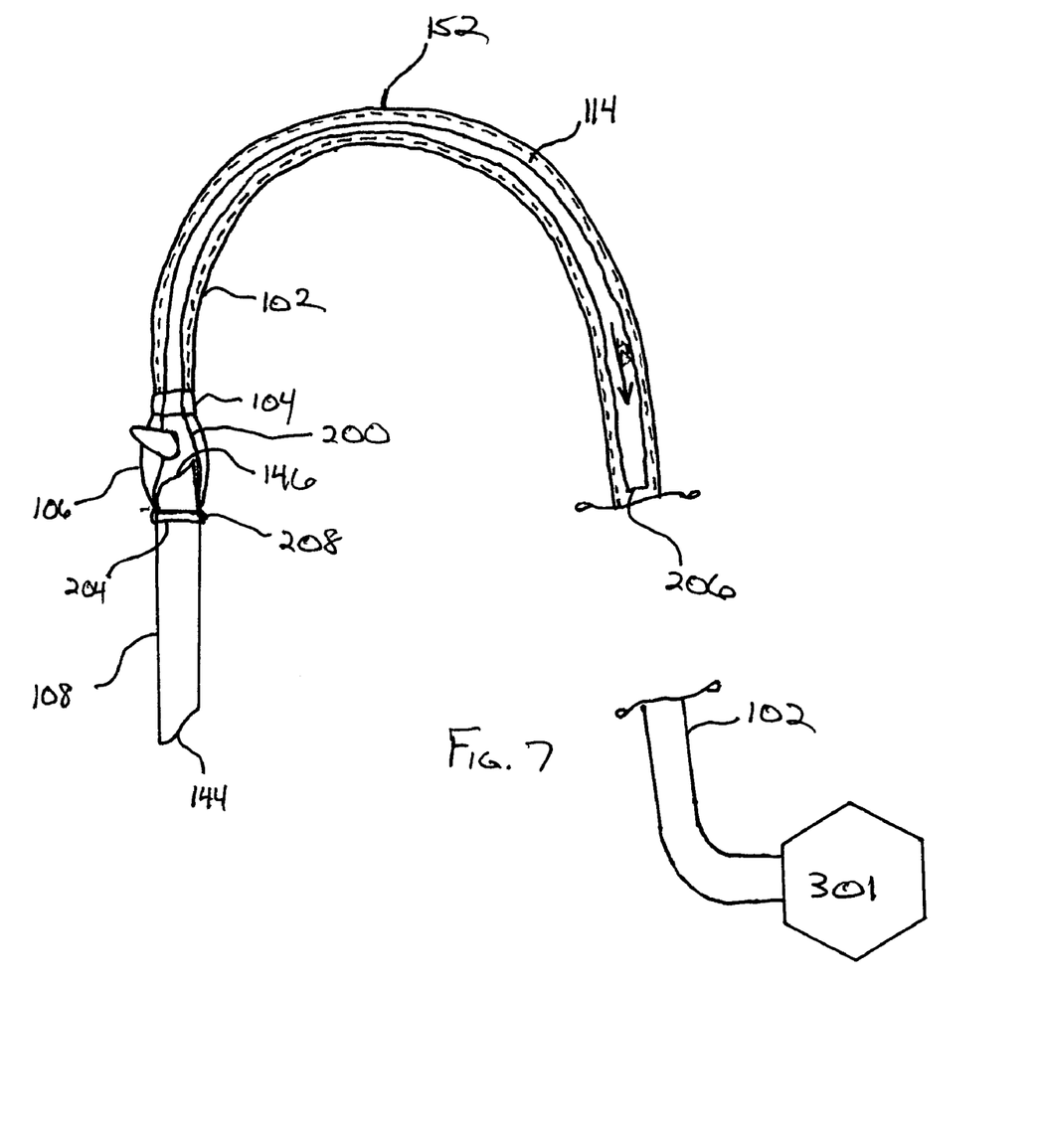
FIG. 7 is a partially hidden, side view of a hand-operable suction device including the backflow resistant evacuator tip of FIG. 4.

Backflow resistant evacuator tip 300 can be used with a suction system 301 as illustrated in FIGS. 5, 6 and 7. Generally, an operator positions backflow resistant evacuator tip 300 such that sleeve exhaust end 206 is positioned proximate and/or within the tip receiving aperture 132 on the control valve 106. Once the sleeve exhaust end 206 is positioned, the operator biases the actuator 136 such that the valve sealing member 138 is in an open configuration with respect to the valve lumen 130. At this point, the vacuum source provides a suction flow as indicated by suction flow arrow 50, which is used to indicate suction flow through all of the referenced drawings, such that the backflow prevention sleeve 200 is directed fully through the valve lumen 130. The sleeve length 210 can be selected such that sleeve exhaust end 206 can pass through valve lumen 130, adapter lumen 120 and ultimately be positioned within the hose lumen 114. Once the backflow prevention sleeve 200 has been received into the control valve 106, the evacuator tip 108 is directed such that exhaust end 146 is seated into the control valve receiving aperture 132. As the evacuator tip 108 is received within the control valve receiving aperture 132, the backflow prevention sleeve 200 forms a seal between the exterior of the evacuator tip 108 and the interior of the tip receiving aperture 132 preventing the introduction of any material into the exhaust end 146 of evacuator tip 108 unless the material has entered the sleeve exhaust end 206 and fully traversed continuous sleeve lumen 202 of the backflow prevention sleeve 200. Upon completion of a dental procedure, the operator can remove and dispose of the backflow resistant (with sleeve) evacuator tip 300 by withdrawing the evacuator tip 108 from the control valve receiver, which simultaneously removes the backflow prevention sleeve 200 from the valve lumen 130.

When backflow resistant evacuator tip 300 is operably attached to control valve 106 as shown in FIGS. 6 and 7, the elastic nature of backflow prevention sleeve 200 causes the backflow prevention sleeve 200 to fully expand to its sleeve length 210 under the influence of the vacuum source. At this point, a continuous suction flow is formed from inlet 144 to sleeve exhaust end 206. Thus, any contaminant matter such as, for example, bodily fluids and particulate waste present within the valve lumen 130, adapter lumen 120 and/or hose lumen 114 and located exterior to the backflow prevention sleeve 200 are physically prevented from entering the evacuator tip 108.

During use of the backflow resistant evacuator tip 300, suction flow can be lost or shut-off in a variety of conditions. For example, an operator can intentionally turn off the suction flow by directing the actuator 136 on control valve 106 to a closed configuration such that valve sealing member 138 closed the valve lumen 130. In other instances, suction flow can be lost by unintentionally blocking the inlet end 144 of evacuator tip 108 such as, for example, with the inner cheek or tongue during a dental procedure, such that further suction flow is prevented. In this instance, a traditional suction device such as, for example, hand-operable suction device 100 can lead to gravity flow of contaminants from any of the vacuum line 102, hose adapter 104, control valve 106, and/or evacuator tip 108 into the work area such as, for example, a patient's mouth in the case of a dental procedure or into a wound or incision in a surgical procedure.

In the case of an intentional closure of control valve 106 when utilizing backflow resistant evacuator tip 300, closure of the valve sealing member 138 causes the closure of the continuous sleeve lumen 202 such that no contaminants are allowed to flow back through backflow prevention sleeve 200. At the same time, the sealing interface between the annular ring 208 and the evacuator tip 108 prevents any contaminants present within the valve lumen 130 from entering the exhaust end 146. Due to the elastic nature of backflow prevention sleeve 200, sealable closure of the valve sealing member 138 within the valve lumen 130 can be accomplished even when backflow prevention sleeve 200 is present. Backflow prevention sleeve 200 can be fabricated so as to be tear-resistant such that normal operation of the control valve 106 does not lead to tearing of the backflow prevention sleeve 200.

In the case of an unintentional loss of suction flow, the elastic, pliable nature of the backflow prevention-sleeve 200 causes the backflow prevention sleeve 200 to collapse such that continuous sleeve lumen 202 is no longer consistently defined. As such, any contaminant matter present within the vacuum line 102, hose adapter 104, and/or control valve 106 must traverse the length of the now collapsed backflow prevention sleeve 200 which cannot be quickly accomplished due to the collapsed nature of the continuous sleeve lumen 202. At the same time, the seal established between the annular ring 208 and evacuator tip 108 continues to exclude the introduction of any contaminant matter exterior to the backflow prevention sleeve 200 into the exhaust end 146 of evacuator tip 108. In some embodiments where vacuum hose 102 is arranged so as to be downwardly directed from above a patient, sleeve length 210 can be selected such that sleeve exhaust end 206 extends beyond a highest elevation 152 such that sleeve exhaust end 206 is downward facing. In this embodiment, contaminant matter does not enter the continuous sleeve lumen 202 as any contaminants present within the vacuum line 102 in proximity to the sleeve exhaust end 206 are directed downward by gravity past the sleeve exhaust end if suction flow is lost, either intentionally or unintentionally.

Figure 8:
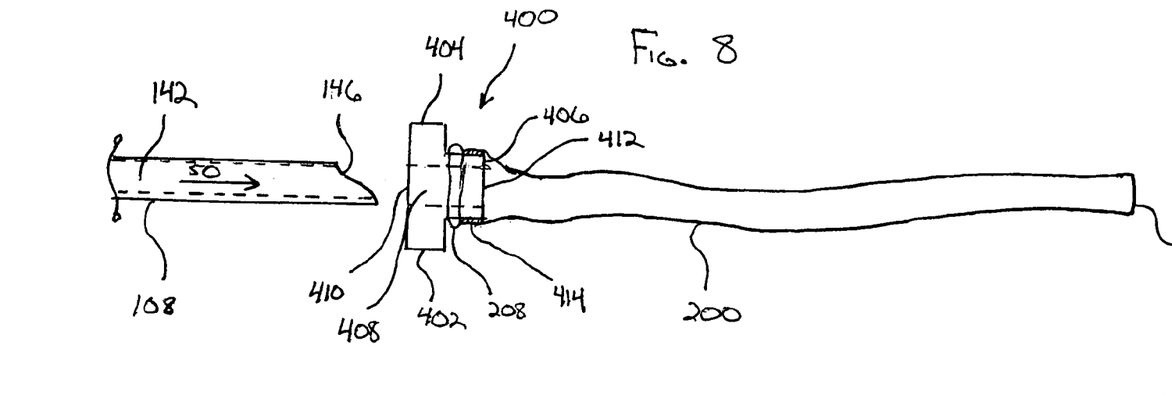
FIG. 8 is a partially hidden, side view of a backflow prevention assembly that stands by itself and can be attached to either a disposable or durable, autoclavable evacuator tip.

An alternative representative embodiment of a backflow prevention assembly 400 is illustrated in FIG. 8. Backflow prevention assembly 400 generally comprises a coupling member 402 and backflow prevention sleeve 200. Coupling member 402 generally comprises a coupling member body 404 having a projecting portion 406. Coupling member 402 further comprises a coupling member lumen 408 operably connecting an adapter aperture 410 and a coupling member valve aperture 412. Backflow prevention sleeve 200 is operably sealed to the coupling member 402 by stretching annular ring 208 over the projecting portion 406. In some embodiments, an adhesive 414 can be used to permanently position the annular ring 208 over the projecting portion 406.

Backflow prevention assembly 400 can be especially advantageous for use in situations in which evacuator tip 108 comprises a reusable, sterilizable evacuator tip. In use, backflow prevention assembly 400 is positioned similarly as previously described with respect to backflow prevention sleeve 200 such that sleeve exhaust end 206 is in proximity to the tip receiving aperture 132 on control valve 106. Actuator 136 is positioned in an open configuration such that the vacuum supply creates a suction flow wherein backflow prevention sleeve 200 is drawn fully into the valve lumen 130. Coupling member 402 can then be attached to the control valve 106 by seating the projecting portion 406 into the tip receiving aperture 132. Next, the sterilizable evacuator tip 108 is attached to the coupling member 402 by slidably inserting the exhaust end 146 into the coupling member ejector aperture 410. When fully assembled, a continuous suction lumen can be defined by the combination of the evacuator tip lumen 142, coupling member lumen 408, sleeve lumen 202, valve lumen 130, adapter lumen 120 and hose lumen 114.

Figure 9:
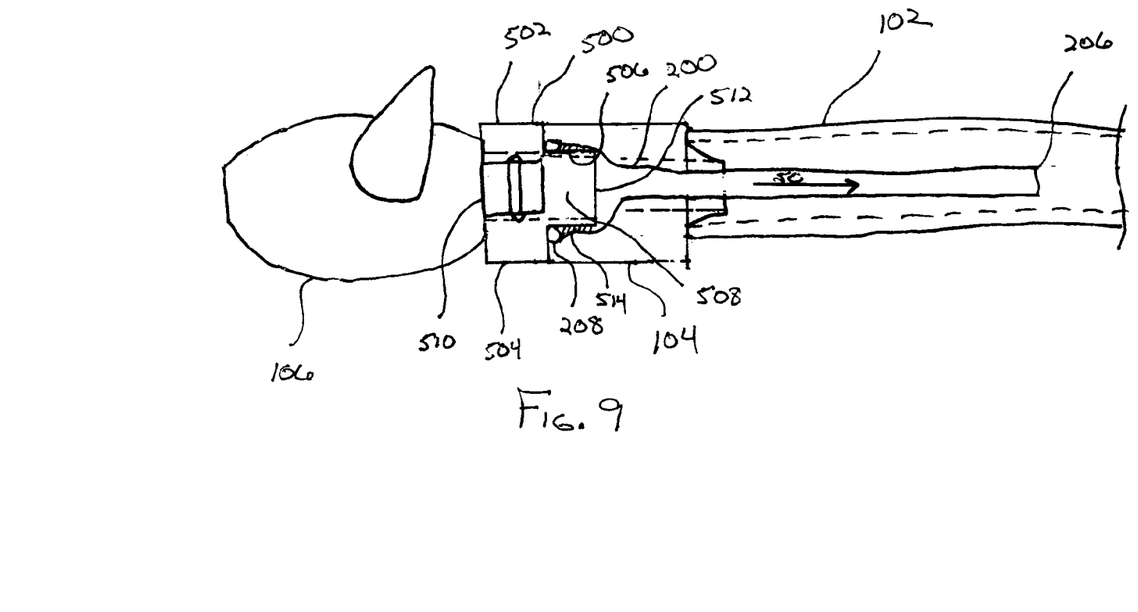
FIG. 9 is a partially hidden, side view of a backflow prevention assembly attaching to the exhaust opening of the control valve and into the vacuum hose.

In an alternative configuration illustrated in FIG. 9, a backflow prevention assembly 500 substantially similar to backflow prevent assembly 400 can be used to locate the backflow prevention sleeve 200 between the control valve 106 and the vacuum hose. Such a configuration can be advantageous when the design of control valve 106, and especially valve sealing member 138, lends itself to tearing the backflow prevention sleeve 200 as actuator 136 is moved between open and closed configurations. Backflow prevention assembly 500 generally comprises a coupling member 502 and backflow prevention sleeve 200. Coupling member 502 generally comprises a coupling member body 504 having a projecting portion 506. Coupling member 502 further comprises a coupling member lumen 508 operably connecting a coupling member valve aperture 510 and a coupling member adapter aperture 512. Backflow prevention sleeve 200 is operably sealingly attached to the coupling member 502 by stretching annular ring 208 over the projecting portion 506. In some embodiments, an adhesive 514 can be used to permanently position the annular ring 208 over the projecting portion 506.

In use, backflow prevention assembly 500 is positioned such that sleeve exhaust end 206 is in proximity to the valve attachment end 124 of the hose adapter 104. Coupling member 502 can then be attached to the hose adapter 104 by slidably inserting the projecting portion 506 into valve attachment end 124. Next, the control valve 106 is attached to the coupling member 502 by slidably inserting the adapter connecting aperture 134 into the coupling member valve aperture 510. When fully assembled, backflow prevention sleeve 200 prevents backflow contamination from the vacuum line 102 and hose adapter 104 from entering the control valve 106.

Figure 10:
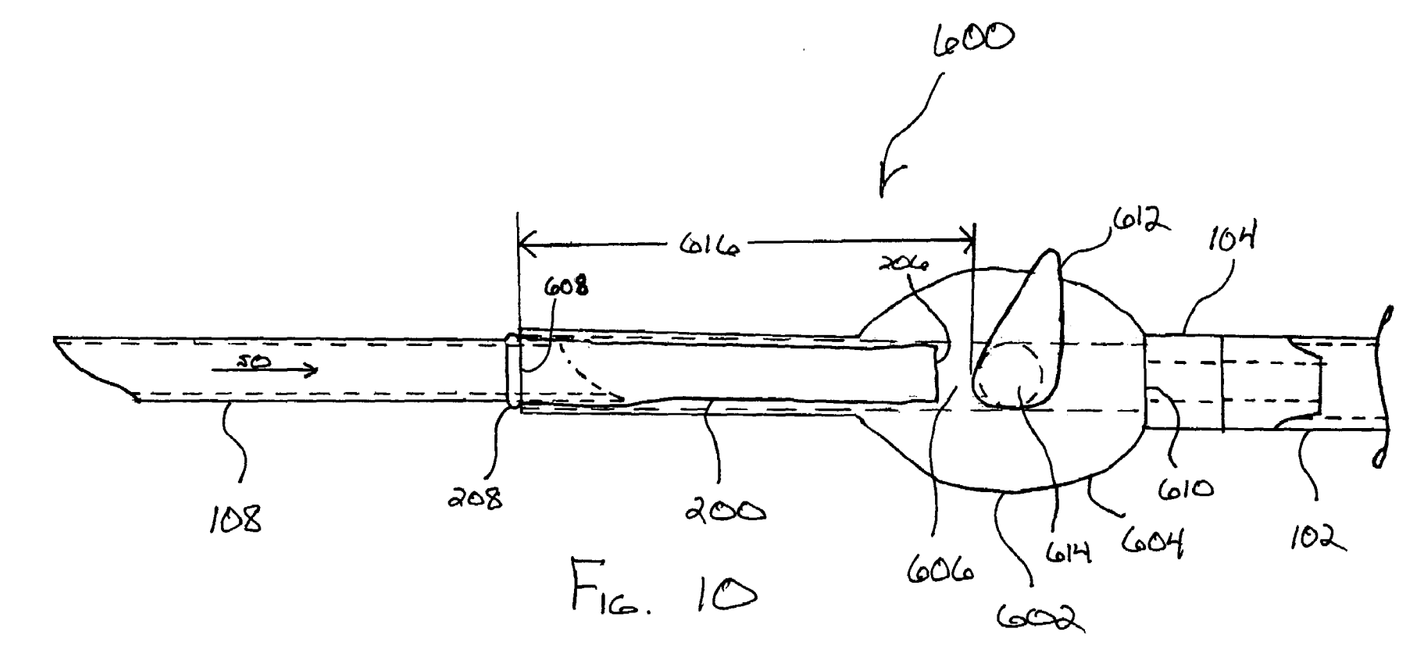
FIG. 10 is a partially hidden, side view of a control valve with an extended receiver for use with the backflow resistant evacuator tip.

In another representative embodiment, as illustrated in FIG. 10, a backflow prevention system 600 can comprise an evacuator tip 108, a backflow prevention sleeve 200, a control valve 602, a hose adapter 104 and a vacuum line 102. Control valve 602 can be fabricated so as to comprise a valve body 604 having a valve lumen 606 defined by an evacuator tip connecting aperture 608 and an adapter connecting aperture 610. Control valve 602 can further comprise an actuator 612 and a valve sealing member 614 to operably open and close the valve lumen 606. As illustrated in FIG. 10, valve body 604 can comprise an ejector interface length 616 defined between the valve sealing member 614 and the ejector connecting aperture 608. As illustrated in FIG. 10, evacuator tip interface length 616 is greater than the sleeve length 210 such that sleeve exhaust end 206 does not reach the valve sealing member 614 when the backflow prevention sleeve 200 is fully extending during suction flow. As such, backflow prevention sleeve 200 does not physically interact with valve sealing member 614 such that valve sealing member 614 cannot tear or rip the backflow prevention sleeve 200 as the actuator 612 is configured between open and closed positions.

Although the present invention has been shown and described with respect to specific details of certain preferred and other important embodiments thereof, it is not intended that such details limit the scope of the invention, taking into consideration reasonable equivalents thereof. Also, the present invention may be used in combination with a plethora of suction devices known in the medical industry.

What is claimed is:

1. A backflow prevention apparatus comprising:
   a flexible sleeve defining a sleeve lumen between a sleeve inlet end and a sleeve exhaust end of the flexible sleeve; and
   a vacuum evacuator tip operably attached to a control valve on a vacuum device, the vacuum evacuator tip defining an evacuator lumen between an evacuator tip inlet end and an evacuator tip exhaust end,
   wherein the sleeve inlet end is adapted for placement over the evacuator tip exhaust end such that a backflow prevention lumen is defined between the evacuator tip inlet end and the sleeve exhaust end; and
   wherein insertion of the evacuator tip exhaust end into a control valve inlet on the control valve causes the flexible sleeve to sealingly engage the control valve inlet, the flexible sleeve being adapted to sealingly close the backflow prevention lumen when the control valve is in a closed disposition.

2. The backflow prevention apparatus of claim 1, wherein the vacuum evacuator tip comprises a single-use, disposable vacuum evacuator.

3. The backflow prevention apparatus of claim 1, wherein the flexible sleeve comprises a single-use disposable flexible sleeve.

4. The backflow prevention apparatus of claim 1, wherein the vacuum evacuator tip is selected from the group comprising: a high-volume evacuator and a saliva ejector (low-volume evacuator).

5. The backflow prevention apparatus of claim 1, wherein the sleeve inlet end is removably placed over the evacuator tip exhaust end.

6. The backflow prevention apparatus of claim 5, wherein the sleeve inlet end comprises an elastic annular ring wherein said elastic annular ring is stretched over the evacuator tip exhaust end wherein said annular ring constricts around the evacuator tip exhaust end to sealingly form the backflow prevention lumen.

7. The backflow prevention apparatus of claim 1, wherein the sleeve inlet end is permanently placed over the evacuator tip exhaust end.

8. The backflow prevention apparatus of claim 7, wherein the sleeve inlet end is adhesively attached to the evacuator tip exhaust end so as to sealingly form the backflow prevention lumen.

9. The backflow prevention apparatus of claim 1, wherein the flexible sleeve comprises a material selected from the group comprising: a natural rubber and a synthetic rubber.

10. The backflow prevention apparatus of claim 1, wherein the flexible sleeve comprises a sleeve length defined between the sleeve inlet end and the sleeve exhaust end, the sleeve length being between about 2 inches to about 30 inches in length.

11. The backflow prevention apparatus of claim 1, wherein the backflow prevention lumen remains open when the vacuum device applies vacuum to the distal end of the sleeve and the control valve is in an open disposition such that a continuous vacuum flow is defined from the evacuator tip inlet end, through the backflow prevention sleeve lumen, through the sleeve exhaust end and into a vacuum hose.

12. The backflow prevention apparatus of claim 1, wherein the vacuum device is selected from the group comprising: a dental vacuum device and a surgical vacuum device.

13. A method for preventing cross-contamination caused by a suction device comprising:
   attaching a barrier sleeve to an evacuator tip of a vacuum evacuator, the barrier sleeve having a continuous barrier lumen adapted to allow vacuum flow upon application of a vacuum, the barrier sleeve being further adapted to prevent exposing a patient to backflow when the vacuum is removed; and
   actuating a valve on the suction device to selectively control application of the vacuum, the barrier sleeve interfacing with the valve such that the continuous barrier lumen is sealingly closed when the valve is in a closed disposition.

14. The method of claim 13, wherein attaching the barrier sleeve to the evacuator tip comprises stretching a sleeve inlet end over an evacuator tip exhaust end.

15. The method of claim 13, wherein attaching the barrier sleeve to the evacuator tip comprises removably attaching the barrier sleeve to the evacuator tip.

16. The method of claim 13, wherein attaching the barrier sleeve to the evacuator tip comprises permanently attaching the barrier sleeve to the evacuator tip.

17. The method of claim 13, further comprising:
   disposing of the barrier sleeve and the vacuum evacuator tip after a single use.

18. The method of claim 13, wherein the vacuum is selected from the group comprising:
   a dental vacuum device and a surgical vacuum device.

19. A suction device for use with a patient comprising:
   a suction system having a vacuum source, a vacuum hose and a control valve;
   a disposable vacuum evacuator tip having an evacuator lumen defined by an evacuator inlet end and an evacuator exhaust end; and
   a backflow prevention sleeve having a sleeve lumen defined by a sleeve inlet end and a sleeve exhaust end;
   wherein the sleeve inlet end is adapted to sealingly attach to the evacuator tip exhaust end such that the evacuator tip lumen and sleeve lumen cooperatively define a backflow prevention lumen;
   wherein the sleeve lumen is sealingly engageable with the control valve; and
   wherein the sleeve exhaust end is positioned within the vacuum hose.

20. The suction device of claim 19, wherein the suction system is selected from the group comprising:
   a dental suction system and a surgical suction system.

21. A backflow prevention apparatus comprising:
   a flexible sleeve defining a sleeve lumen between a sleeve inlet end and a sleeve exhaust end of the flexible sleeve; and
   a vacuum evacuator tip defining an evacuator lumen between an evacuator tip inlet end and an evacuator tip exhaust end,
   wherein the sleeve inlet end is adapted for placement over the evacuator tip exhaust end such that a backflow prevention lumen is defined between the evacuator tip inlet end and the sleeve exhaust end;
   wherein a vacuum flow from the evacuator tip inlet end to the sleeve exhaust end is allowed through the backflow prevention lumen upon application of vacuum to the sleeve exhaust end and a reverse flow from the sleeve exhaust end to the evacuator tip inlet is prevented when vacuum is not applied to the sleeve exhaust end, and wherein the evacuator tip exhaust end is inserted into a valve inlet on a vacuum control valve such that that the flexible sleeve sealingly engages against the valve inlet.

22. The backflow prevention apparatus of claim 21, wherein actuation of the vacuum control valve to a closed disposition sealingly closes the backflow prevention lumen.

* * * * *